(12) United States Patent
Kim et al.

(10) Patent No.: US 6,357,284 B1
(45) Date of Patent: Mar. 19, 2002

(54) CERAMIC CORROSION POTENTIAL SENSOR AND METHOD FOR ITS MANUFACTURE

(75) Inventors: Young-Jin Kim, Clifton Park; Minyoung Lee, Niskayuna, both of NY (US); Samson Hettiarachchi, Menlo Park, CA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/389,882

(22) Filed: Sep. 3, 1999

(51) Int. Cl.[7] ............................................. G01M 27/26

(52) U.S. Cl. ........................................ 73/86; 204/435

(58) Field of Search ......................... 73/86; 204/280, 204/286, 404, 422, 423, 435; 376/305, 249

(56) References Cited

U.S. PATENT DOCUMENTS

| 5,234,570 A | * | 8/1993 | Taylor et al. |
| 5,238,553 A | * | 8/1993 | Hettiarachchi et al. |
| 5,571,394 A | * | 11/1996 | Hettiarachchi et al. |
| 5,896,432 A | | 4/1999 | Kim et al. |

* cited by examiner

Primary Examiner—Robert Raevis
(74) Attorney, Agent, or Firm—Noreen C. Johnson; Christian G. Cabou

(57) ABSTRACT

A ceramic sensor is disclosed that includes a ceramic tube having a closed end and an open end, and a metal sleeve having open first and second ends. The ceramic tube is formed of stabilized zirconia. The metal sleeve extends about the open end of the ceramic tube and is sealingly joined thereto at a contact region by a brazeless bond resulting from hot isostatic pressing. A mixture of metal and metal oxide powders is provided within the ceramic tube adjacent the closed end, and a conducting wire extends from the mixture of metal and metal oxide powders to the second end of the metal sleeve.

15 Claims, 3 Drawing Sheets

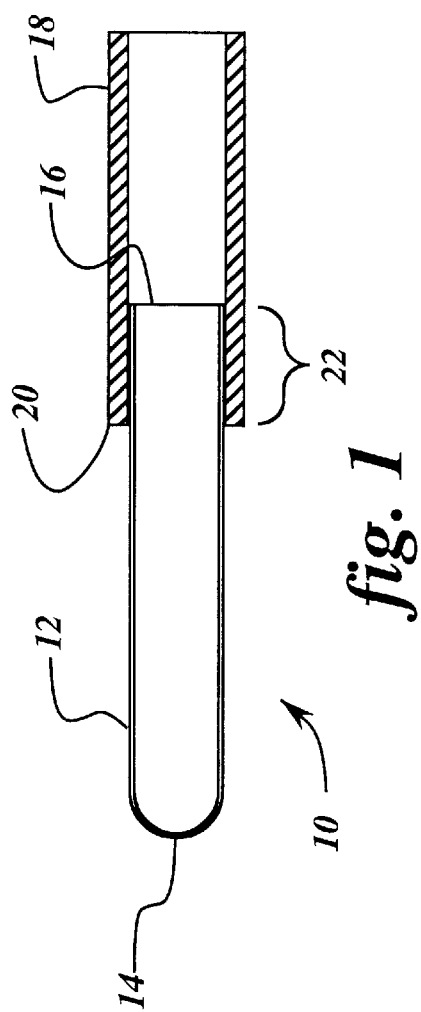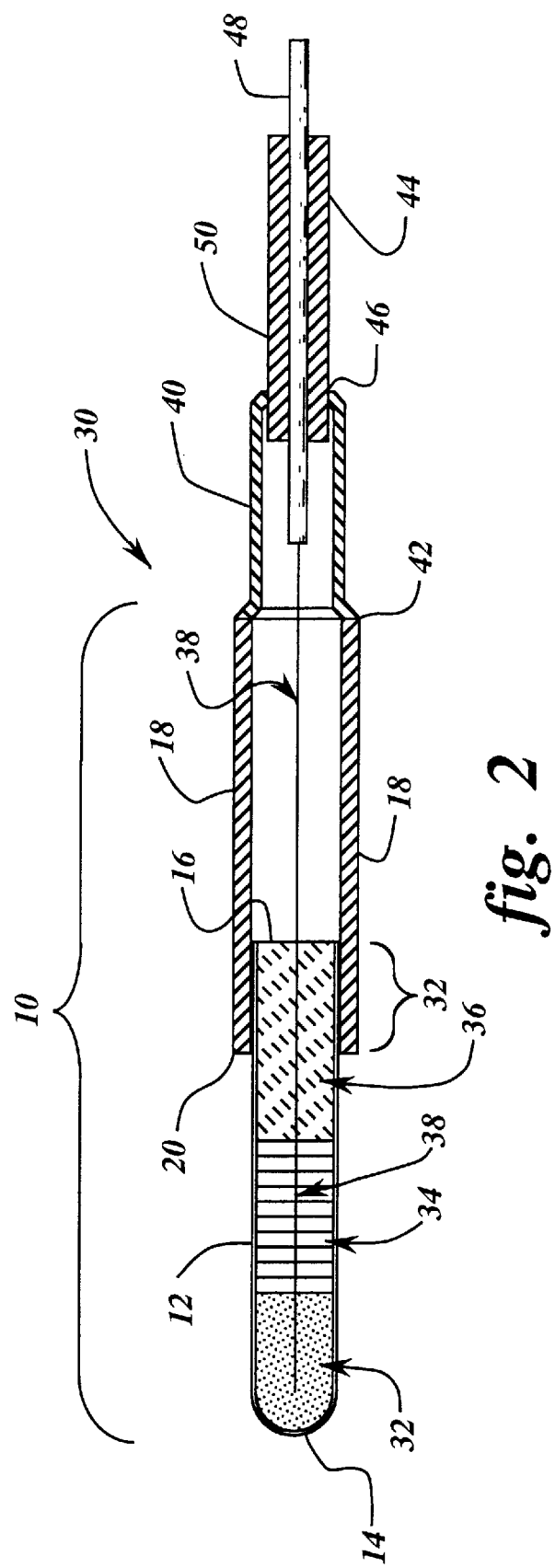

CERAMIC CORROSION POTENTIAL SENSOR AND METHOD FOR ITS MANUFACTURE

BACKGROUND OF THE INVENTION

Nuclear reactors are typically in the form of a boiling water reactor having suitable nuclear fuel disposed in a reactor pressure vessel in which water is heated. The water and steam are carried through various components and piping which are typically formed of stainless steel, with other materials such as alloy 182 weld metal and alloy 600 being used for various components directly inside the reactor pressure vessel.

Materials in the reactor core region are susceptible to irradiation assisted stress corrosion cracking. This is because the material in the core region is exposed to the highly oxidizing species generated by the radiolysis of water by both gamma and neutron radiation under normal water chemistry conditions, in addition to the effect of direct radiation assisted stress corrosion cracking. The oxidizing species increases the electrochemical corrosion potential of the material which in turn increases its propensity to undergo intergranular stress corrosion cracking or irradiation assisted stress corrosion cracking.

Suppression of the oxidizing species carried within such materials is desirable in controlling intergranular stress corrosion cracking. An effective method of suppressing the oxidizing species coming into contact with the material is to inject hydrogen into the reactor water via the feedwater system so that recombination of the oxidants with hydrogen occurs within the reactor circuit.

This method is called hydrogen water chemistry and is widely practiced for mitigating intergranular stress corrosion cracking of materials in boiling water reactors. When hydrogen water chemistry is practiced in a boiling water reactor, the electrochemical corrosion potential of the stainless steel material decreases from a positive value generally in the range of 0.050 to 0.200 V (SHE) under normal water chemistry to a value less than −0.230 V (SHE), where SHE stands for the Standard Hydrogen Electrode potential. When the electrochemical corrosion potential is below this negative value, intergranular stress corrosion cracking of stainless steel can be mitigated and its initiation can be prevented.

Considerable efforts have been made in the past decade to develop reliable electrochemical corrosion potential sensors to be used as reference electrodes which can be used to determine the electrochemical corrosion potential of operating surfaces of components.

The typical electrochemical corrosion potential sensor experiences a severe environment in view of the temperature of the water well exceeding 88° C.; relatively high flow rates of the water up to and exceeding several m/s; and the high nuclear radiation in the core region.

A drawback of currently available sensors is that they have a limited lifetime in that some have failed after only three months of use while a few have shown evidence of operation for approximately six to nine months. Two major modes of sensor failure have been the cracking and corrosive attack in a ceramic-to-metal braze used at the sensing tip, and the dissolution of a sapphire insulating ceramic material used to electrically isolate the sensing tip from the metal conductor cable for platinum and stainless steel type sensors.

Accordingly, it is desired to improve electrochemical corrosion potential sensors in terms of durability and longevity.

SUMMARY OF THE INVENTION

A ceramic sensor is provided that includes a ceramic tube having a closed end and an open end, and a metal sleeve having open first and second ends. The ceramic tube is formed of stabilized zirconia. The metal sleeve extends about the open end of the ceramic tube and is sealingly joined thereto at a contact region by a brazeless bond resulting from hot isostatic pressing. A mixture of metal and metal oxide powders is provided within the ceramic tube adjacent the closed end, and a conducting wire extends from the mixture of metal and metal oxide powders to the second end of the metal sleeve.

In another embodiment of the present invention, a method for providing a ceramic sensor calls for inserting the ceramic tube into the metal sleeve, and executing a hot isostatic pressing step, in an environment and at a temperature and a pressure sufficient to form a sealed joint therebetween at said contact region to form a brazeless casing. The ceramic sensor is then completed.

DESCRIPTION OF DRAWINGS

Preferred embodiments of the present invention will be described in detail below with reference to the accompanying drawings in which:

FIG. 1 is an axial section through a brazeless casing for a brazeless ceramic sensor according to an embodiment of the present invention;

FIG. 2 is an axial section through a brazeless ceramic sensor according to an embodiment of the present invention;

DESCRIPTION OF PREFERRED EMBODIMENTS

Figure 3:
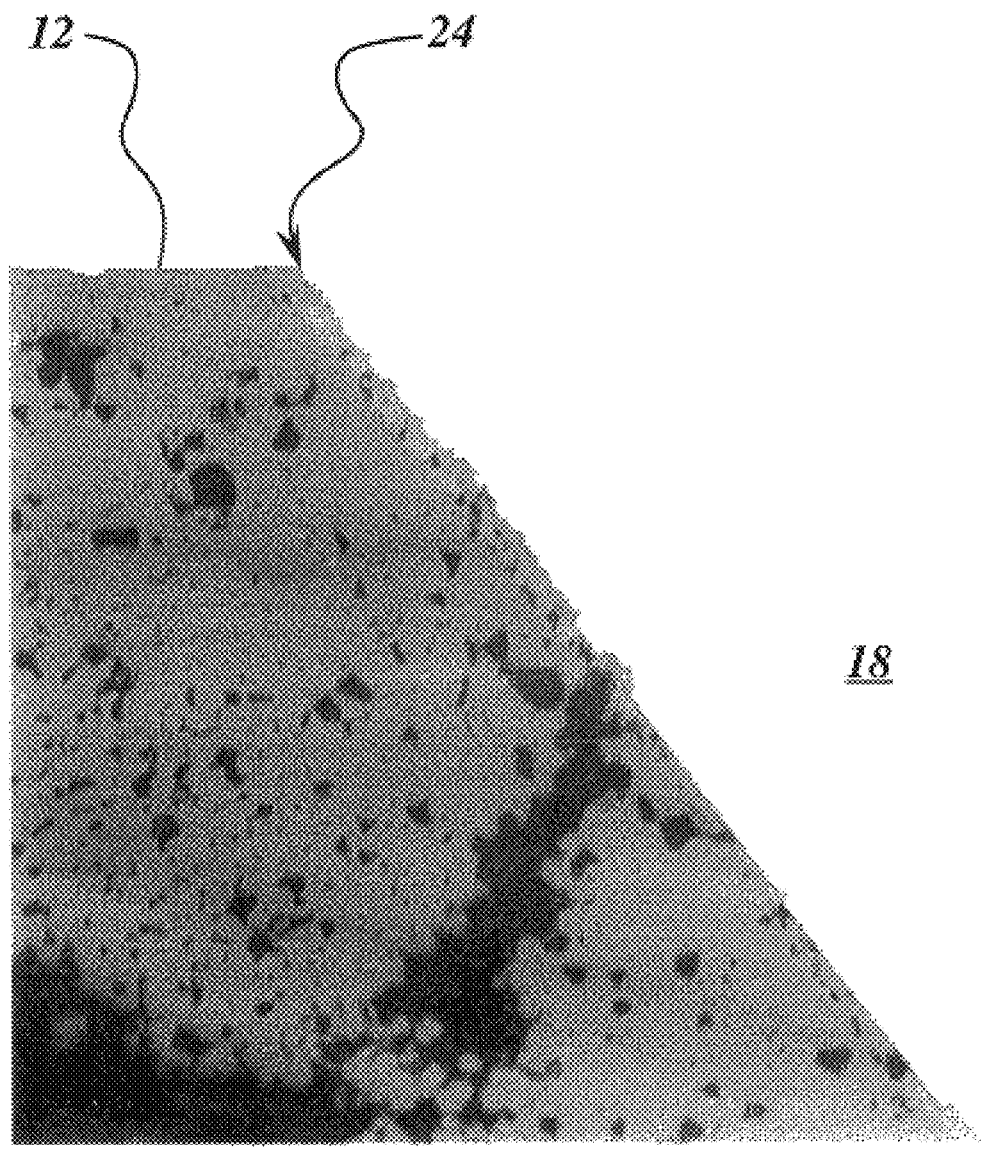
FIG. 3 is a photomicrograph illustrating a brazeless bond between a ceramic tube and a metal sleeve of a brazeless ceramic sensor produced in accordance with an embodiment of the present invention.

A brazeless casing for a ceramic sensor is generally indicated by reference 10 in FIG. 1. The casing 10 includes a ceramic tube 12 having a closed end 14 and an open end 16. The ceramic selected for the tube should be capable of surviving without dissolution in a boiling water reactor environment having high temperature water at relatively high flow rates. The ceramic should also be an ionic conductor at reactor operating temperatures. Stabilized zirconia is a suitable material. The zirconia is typically stabilized with an oxide such as yttria, magnesia, calcia, and ceria. Yttria and magnesia are the most typical stabilizing agents.

A metal sleeve 18, typically of 316 stainless steel or alloy 42 has an open first end 20 extending about the open end 16 of the ceramic tube 12. The inside diameter of the metal sleeve 18 at the first end 20 closely matches the outside diameter of the open end 16 of the ceramic tube 12. The ceramic tube 12 and metal sleeve 18 overlap over a contact region 22. The ceramic tube 12 would generally be inserted into the metal sleeve 18, but the reverse is also feasible (i.e., having the sleeve 18 of smaller diameter and inserting the first end 20 of the metal sleeve 18 into the open end 16 of the ceramic tube 12).

The ceramic tube 12 and the metal sleeve 18 are joined over the contact region 22 by a hot isostatic pressing process which causes diffusion bonding between the ceramic tube 12 and metal resulting in a brazeless seal therebetween.

Typical hot isostatic pressing conditions include a temperature ranging from about 900 to about 1300° C., a pressure on the order of about 100 to 400 MPa, in an inert gas environment such as argon.

FIG. 3 is a photomicrograph illustrating the interfacial morphology 24 of a typical diffusion bond formed between an yttria stabilized zirconia ceramic tube 12 and a 316 stainless steel metal sleeve 18 formed at 1200° C. for 1 hour at 30,000 psi (210 MPa).

FIG. 2 illustrates a brazeless ceramic sensor 30 which incorporates a brazeless casing 10 as described above. A mixture of metal and metal oxide powders 32 is packed into the ceramic tube 12 adjacent its closed end 14. The powders may be $Fe/Fe_3O_4$, $Cu/Cu_2O$ and Ni/NiO.

Sealing parts 34 are inserted into the ceramic tube 12 adjacent the powders 32 to keep the powders 32 in place. The sealing parts 34 may be discs of polytetrafluoroethylene (such as sold under the trademark TEFLON by Dupont).

Ceramic insulating packing materials 36 are inserted in the ceramic tube 12 behind the packing pieces 34 to contain the packing pieces 34 and to provide further insulation. The ceramic insulating packing materials 36 may be a ceramic fiber such as glass wool.

A conducting wire 38 extends from within the powder 32, substantially the length of the ceramic casing 10. The conducting wire 38 is of a metal which contains as its principle component, the metal of the powders 32. For example, a stainless steel wire would be selected for a $Fe/Fe_3O_4$ powder, copper wire would be selected for a $Cu/Cu_2O$ powder, and nickel wire for a Ni/NiO powder.

A stainless steel transition piece 40 is welded to the metal sleeve 18 adjacent an open second end 42 of the metal sleeve 18. The transition piece 40 extends between the second end 42 of the metal sleeve 18 and a mineral insulated ("MI") cable 44. The transition piece 40 is sealingly joined to the MI cable by a suitable joining method such as brazing at reference 46.

The MI cable has a central conductor 48 which is joined to the conducting wire 38 for electrical communication therewith by suitable means such as spot welding. The MI cable has an insulating sleeve 50 of a suitable mineral oxide such as alumina ($Al_2O_3$).

Figure 4:
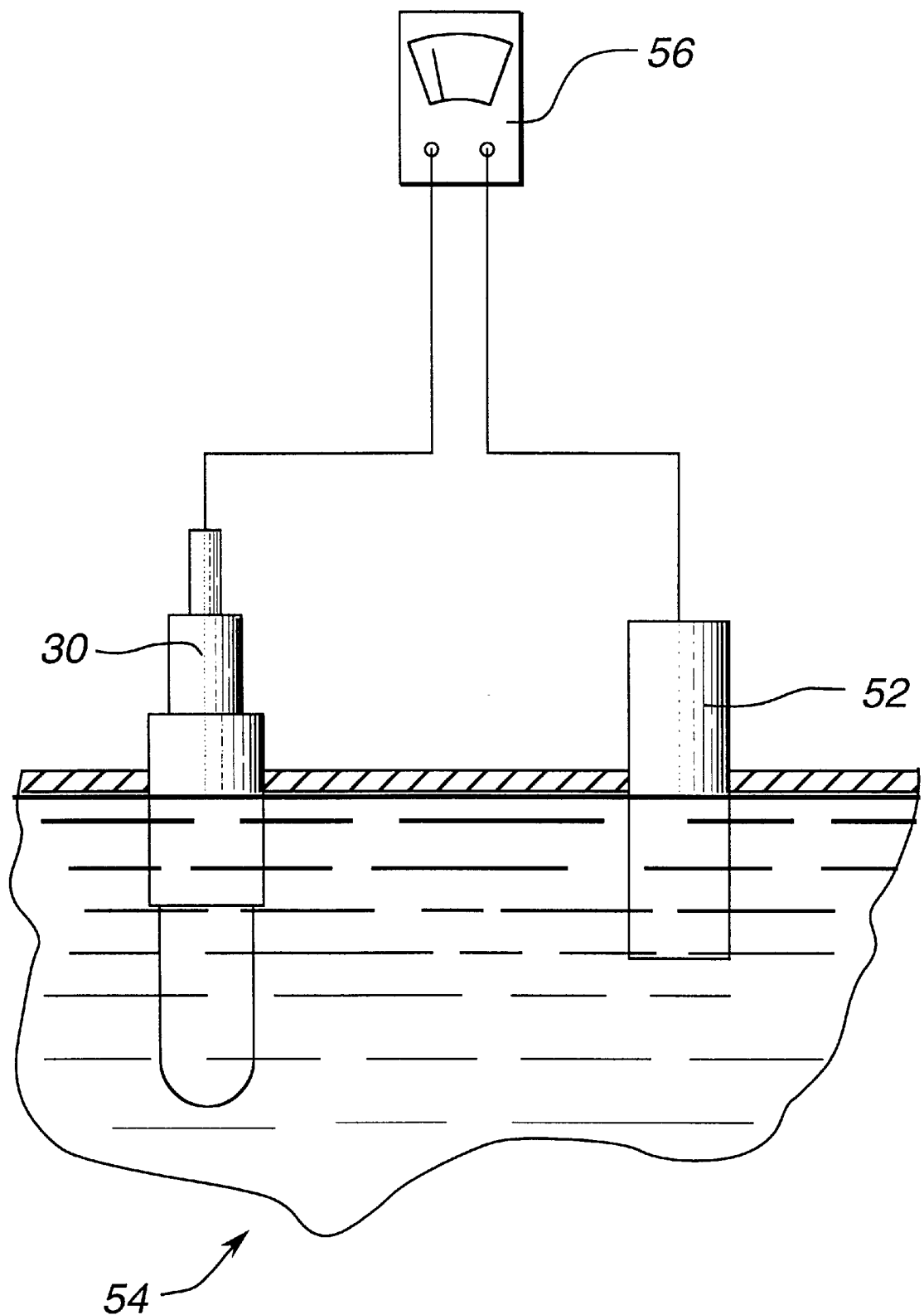
FIG. 4 is a schematic illustration of a ceramic sensor in use according to an embodiment of the present invention.

FIG. 4 illustrates a typical ceramic sensor 30 in use. The ceramic sensor 30 functions as a reference electrode, and is coupled to a platinum (measurement) electrode 52 situated elsewhere in a reactor circuit 54 through a potentiometer 56. Knowing the reactor water conditions such as temperature and pH, the potentiometer readings may be used to calculate the electrochemical corrosion potential.

The above description is intended in an illustrative rather than a restrictive sense. Variations may be apparent to persons skilled in the art without departing from the scope of the invention as defined by the claims set out below.

We claim:

1. A ceramic sensor comprising:
   a ceramic tube comprising stabilized zirconia having a closed end and an open end;
   a metal sleeve having open first and second ends, said first end of said metal sleeve extending about said open end of said ceramic tube and being sealingly joined thereto at a contact region by a brazeless bond resulting from hot isostatic pressing;
   a mixture of metal and metal oxide powders within said ceramic tube adjacent said closed end;
   a conducting wire extending from said mixture of metal and metal oxide powders to said second end of said metal sleeve.

2. The ceramic sensor of claim 1, further comprising sealing parts adjacent said mixture of metal and metal oxide powders.

3. The ceramic sensor of claim 2, wherein the sealing parts comprise a polymer.

4. The ceramic sensor of claim 3, wherein the polymer comprises polytetraflouroethylene.

5. The ceramic sensor of claim 2, further comprising ceramic insulating packing materials adjacent said sealing parts.

6. The ceramic sensor of claim 5, wherein the insulating packing materials comprise glass wool.

7. The ceramic sensor of claim 1 wherein:
   said metal sleeve is joined by welding to a transition piece extending away from said closed end of said ceramic tube;
   said transition piece is sealingly joined about a mineral insulated cable; and
   said mineral insulated cable has a central conductor which is joined to said conducting wire for electrical communication therewith.

8. The ceramic sensor of claim 1 wherein said mixture of metal and metal oxide powders is selected from the group consisting of $Fe/Fe_3O_4$, $Cu/Cu_2O$ and Ni/NiO.

9. The ceramic sensor of claim 8, wherein the conducting wire comprises a metal from the group consisting of Fe, Cu, and Ni.

10. The ceramic sensor of claim 1, wherein the zirconia is stabilized with yttria or magnesia.

11. The ceramic sensor of claim 1, wherein said metal sleeve comprises 316 stainless steel or alloy 42.

12. The ceramic sensor of claim 1, wherein said metal sleeve is disposed radially outwardly of said ceramic tube.

13. A ceramic sensor comprising:
    a ceramic tube comprising stabilized zirconia having a closed end and an open end;
    a metal sleeve having open first and second ends, said first end of said metal sleeve extending about said open end of said ceramic tube and being sealingly joined thereto at a contact region by a brazeless bond resulting from hot isostatic pressing;
    a mixture of metal and metal oxide powders within said ceramic tube adjacent said closed end, said mixture of metal and metal oxide powders comprising Cu/CuO;
    sealing parts adjacent said mixture of metal and metal oxide powders;
    a conducting wire extending from said mixture of metal and metal oxide powders to said second end of said metal sleeve.

14. A method of fabricating a brazeless ceramic sensor, said method comprising the steps of:
    obtaining a ceramic tube having a closed end and an open end, said ceramic tube comprising stabilized zirconia;
    obtaining a metal sleeve having open first and second ends;
    inserting said open end of said ceramic tube into said first end of said metal sleeve to overlap over a contact region;
    subjecting said ceramic tube and metal sleeve to hot isostatic pressing in an environment and at a temperature and a pressure sufficient to form a sealed joint therebetween at said contact region to form a brazeless casing;
    inserting a conducting wire into said casing substantially to said closed end of said ceramic tube;
    packing said closed end with a mixture of metal and metal oxide powders, said conducting wire extending into said mixture of metal and metal oxide powders.

15. The method of claim 14, wherein said hot isostatic pressing is carried out in an inert atmosphere at a temperature of from about 900 to about 1300° C. at a pressure of about 100 to about 400 MPa.

* * * * *